US006967089B1

(12) United States Patent
Keegan et al.

(10) Patent No.: US 6,967,089 B1
(45) Date of Patent: Nov. 22, 2005

(54) DELIVERY SYSTEM FOR PORCINE SOMATOTROPIN

(75) Inventors: Mitchell Keegan, Werrington (AU); Mark Richard Jones, Tennyson (AU); Geoffrey Philip M. Moore, Summer Hill (AU)

(73) Assignees: Commonwealth Scientific and Industrial Research Organisation, Australian Capital Territory (AU); University of Western Sydney (Nepean), New South Wales (AU); Pig Research and Development Corporation, Australian Capital Territory (AU)

(*) Notice: Subject to any disclaimer, the term of this patent is extended or adjusted under 35 U.S.C. 154(b) by 0 days.

(21) Appl. No.: 09/807,519

(22) PCT Filed: Oct. 18, 1999

(86) PCT No.: PCT/AU99/00896

§ 371 (c)(1), (2), (4) Date: Sep. 17, 2001

(87) PCT Pub. No.: WO00/23601

PCT Pub. Date: Apr. 27, 2000

(30) Foreign Application Priority Data

Oct. 16, 1998 (AU) .............................................. PP6556

(51) Int. Cl.[7] ......................... C12P 21/06; C12N 15/00; C12N 5/00; C12N 16/63; C07H 21/04

(52) U.S. Cl. ................... 435/69.1; 435/320.1; 435/325; 435/455; 435/377; 536/24.1

(58) Field of Search ............................. 435/69.1, 320.1, 435/325, 455, 377; 536/24.1; 800/4

(56) References Cited

U.S. PATENT DOCUMENTS

| | | | | |
|---|---|---|---|---|
| 4,923,808 A | | 5/1990 | Matteucci | |
| 4,992,367 A | | 2/1991 | Cullen | |
| 5,082,783 A | * | 1/1992 | Ernst et al. | 435/69.1 |
| 5,641,665 A | | 6/1997 | Hobart et al. | |
| 5,681,562 A | | 10/1997 | Sobol et al. | |
| 5,681,818 A | | 10/1997 | Spencer et al. | |
| 5,759,578 A | | 6/1998 | Soon-Shiong et al. | |
| 5,856,159 A | | 1/1999 | Perez | |
| 5,858,751 A | * | 1/1999 | Paulson et al. | 435/193 |
| 5,879,709 A | | 3/1999 | Soon-Shiong et al. | |
| 5,932,211 A | | 8/1999 | Wilson et al. | |
| 6,147,055 A | | 11/2000 | Hobart et al. | |
| 2003/0104578 A1 | * | 6/2003 | Ballance | 435/69.4 |

OTHER PUBLICATIONS

O'Mahony et al. 1989, Animal Genetics, vol. 20, No. 3, p. 313–316.*
Anson D.S. et al., Biochem. J. (1992) 284, 789–794.
Fakhrai H. et al, Journal of Immunotherapy (1997) 20(6): 437–448.
Cullen B.R., (1986) Cell vol. 46:973–982.

"Expression of a Cloned Human Interleukin–2 cDNA is Enhanced by the Substitution of a Heterologous mRNA Leader Region", B.R. Cullen, DNA, vol. 7, No. 9, 1988, pp. 645–650.

Tai It et al., "Microencapsulation of recombinant cells: a new delivery system for gene therapy", Aug. 1993, 7(11): 1061–9.

"Nucleotide Sequence of Human Preproinsulin Complementary DNA", Science, vol. 208, Apr. 4, 1980, pp. 57–59.

* cited by examiner

*Primary Examiner*—Gerry Leffers
*Assistant Examiner*—Maria Marvich
(74) *Attorney, Agent, or Firm*—McDermott Will & Emery LLP

(57) ABSTRACT

An expression construct is disclosed which is useful for delivering mature somatotropin to a host. Mature somatotropin is operably linked to an insulin secretory signal. Host cells comprising the expression cassette are cultured under conditions enabling the expression and secretion of somatotropin.

9 Claims, 13 Drawing Sheets

FIGURE 1: ISS-pST gene construct

Figure 3:
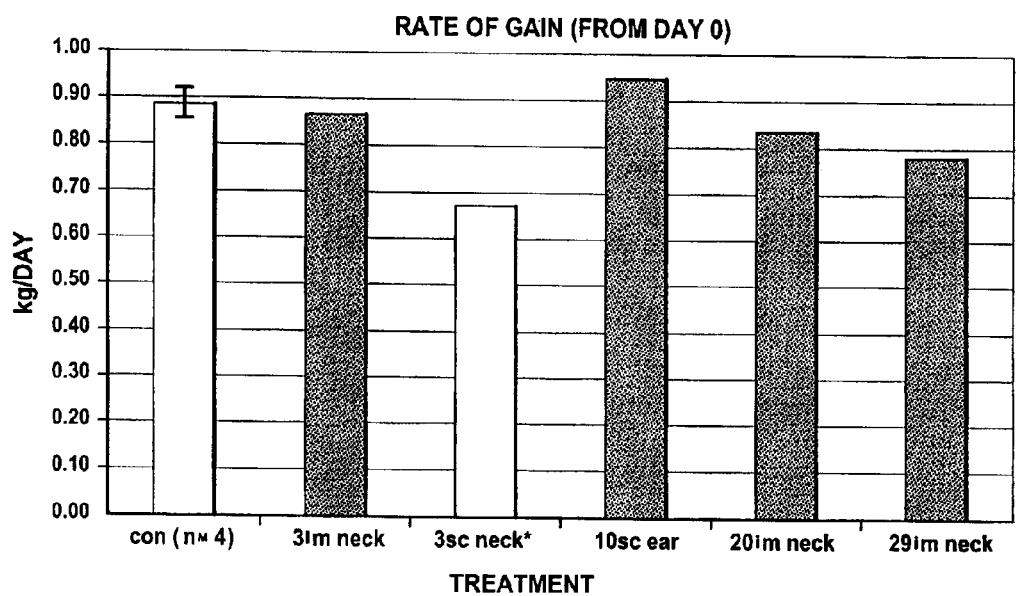

```
  1 GCTAGCATGG CCCTGTGGAT GCGCCTCCTG CCCCTGCTGG CGCTGCTGGC
 51 CCTCTGGGGA CCTGACCCAG CCGCAGCCCT CGAGATGTTT CCAGCTATGC
101 CACTTTCTTC TCTGTTCGCT AACGCTGTTC TTCGGGCCCA GCACCTGCAC
151 CAACTGGCTG CCGACACCTA CAAGGAGTTT GAGCGCGCCT ACATCCCGGA
201 GGGACAGAGG TACTCCATCC AGAACGCCCA GGCTGCCTTC TGCTTCTCGG
251 AGACCATCCC GGCCCCCACG GGCAAGGACG AGGCCCAGCA GAGATCGGAC
301 GTGGAGCTGC TGCGCTTCTC GCTGCTGCTC ATCCAGTCGT GGCTCGGGCC
351 CGTGCAGTTC CTCAGCAGGG TCTTCACCAA CAGCCTGGTG TTTGGCACCT
401 CAGACCGCGT CTACGAGAAG CTGAAGGACC TGGAGGAGGG CATCCAGGCC
451 CTGATGCGGG AGCTGGAGGA TGGCAGCCCC CGGGCAGGAC AGATCCTCAA
501 GCAAACCTAC GACAAATTTG ACACAAACTT GCGCAGTGAT GACGCGCTGC
551 TTAAGAACTA CGGGCTGCTC TCCTGCTTCA AGAAGGACCT GCACAAGGCT
601 GAGACATACC TGCGGGTCAT GAAGTGTCGC CGCTTCGTGG AGAGCAGCTG
651 TGCCTTCTAG TCTAGA    (SEQ ID NO:3)
```

ATG...GCC- insulin secretory signal.

GCTAGC- *Nhe* I restriction site incorporated into construct in order to ligate into plasmid.

CTCGAG- *Xho* I restriction site incorporated into construct in order to ligate secretory signal and pST.

TCTAGA- *Xba* I restriction site incorporated into construct in order to ligate into plasmid.

FIGURE 2: ISS-pST peptide sequence.

```
  1  MALWMRLLPL LALLALWGPD PAAALEMFPA MPLSSLFANA VLRAQHLHQL
 51  AADTYKEFER AYIPEGQRYS IQNAQAAFCF SETIPAPTGK DEAQQRSDVE
101  LLRFSLLLIQ SWLGPVQFLS RVFTNSLVFG TSDRVYEKLK DLEEGIQALM
151  RELEDGSPRA GQILKQTYDK FDTNLRSDDA LLKNYGLLSC FKKDLHKAET
201  YLRVMKCRRF VESSCAF     (SEQ ID NO:2)
```

MAL....AAA- insulin secretory signal, cleaved upon secretion of pST.
LE- function of XhoI cleavage site; result in no predicted secondary structural changes to pST.

Plate 1
Plate 2
Fig. 6

SEQUENCE LISTING

<160> NUMBER OF SEQ ID NOS: 4

<210> SEQ ID NO 1
<211> LENGTH: 24
<212> TYPE: PRT
<213> ORGANISM: Homo Sapien

<400> SEQUENCE: 1

Met Ala Leu Trp Met Arg Leu Leu Pro Leu Leu Ala Leu Leu Ala Leu
1               5                   10                  15

Trp Gly Pro Asp Pro Ala Ala Ala
            20

<210> SEQ ID NO 2
<211> LENGTH: 72
<212> TYPE: DNA
<213> ORGANISM: Homo Sapien

<400> SEQUENCE: 2
atggccctgt ggatgcgcct cctgcccctg ctggcgctgc tggccctctg gggacctgac      60
ccagccgcag cc                                                         72

<210> SEQ ID NO 3
<211> LENGTH: 217
<212> TYPE: PRT
<213> ORGANISM: Artificial Sequence
<220> FEATURE:
<223> OTHER INFORMATION: Unknown Organsim

<400> SEQUENCE: 3

Met Ala Leu Trp Met Arg Leu Leu Pro Leu Leu Ala Leu Leu Ala Leu
1               5                   10                  15

Trp Gly Pro Asp Pro Ala Ala Ala Leu Glu Met Phe Pro Ala Met Pro
            20                  25                  30

Leu Ser Ser Leu Phe Ala Asn Ala Val Leu Arg Ala Gln His Leu His
        35                  40                  45

Gln Leu Ala Ala Asp Thr Tyr Lys Glu Phe Glu Arg Ala Tyr Ile Pro
    50                  55                  60

Glu Gly Gln Arg Tyr Ser Ile Gln Asn Ala Gln Ala Ala Phe Cys Phe
65                  70                  75                  80

Ser Glu Thr Ile Pro Ala Pro Thr Gly Lys Asp Glu Ala Gln Gln Arg
                85                  90                  95

Ser Asp Val Glu Leu Leu Arg Phe Ser Leu Leu Ile Gln Ser Trp
            100                 105                 110

Leu Gly Pro Val Gln Phe Leu Ser Arg Val Phe Thr Asn Ser Leu Val
        115                 120                 125

Phe Gly Thr Ser Asp Arg Val Tyr Glu Lys Leu Lys Asp Leu Glu Glu
    130                 135                 140

Gly Ile Gln Ala Leu Met Arg Glu Leu Glu Asp Gly Ser Pro Arg Ala
145                 150                 155                 160

Gly Gln Ile Leu Lys Gln Thr Tyr Asp Lys Phe Asp Thr Asn Leu Arg
                165                 170                 175

Ser Asp Asp Ala Leu Leu Lys Asn Tyr Gly Leu Leu Ser Cys Phe Lys
            180                 185                 190

Lys Asp Leu His Lys Ala Glu Thr Tyr Leu Arg Val Met Lys Cys Arg
        195                 200                 205

```
Arg Phe Val Glu Ser Ser Cys Ala Phe
    210                 215

<210> SEQ ID NO 4
<211> LENGTH: 666
<212> TYPE: DNA
<213> ORGANISM: Artificial Sequence
<220> FEATURE:
<223> OTHER INFORMATION: Unknown Organism

<400> SEQUENCE: 4
gctagcatgg ccctgtggat gcgcctcctg cccctgctgg cgctgctggc cctctgggga      60
cctgacccag ccgcagccct cgagatgttt ccagctatgc cactttcttc tctgttcgct     120
aacgctgttc ttcgggccca gcacctgcac caactggctg ccgacaccta caaggagttt     180
gagcgcgcct acatcccgga gggacagagg tactccatcc agaacgccca ggctgccttc     240
tgcttctcgg agaccatccc ggcccccacg ggcaaggacg aggcccagca gagatcggac     300
gtggagctgc tgcgcttctc gctgctgctc atccagtcgt ggctcgggcc cgtgcagttc     360
ctcagcaggg tcttcaccaa cagcctggtg tttggcacct cagaccgcgt ctacgagaag     420
ctgaaggacc tggaggaggg catccaggcc ctgatgcggg agctggagga tggcagcccc     480
cgggcaggac agatcctcaa gcaaacctac gacaaatttg acacaaactt gcgcagtgat     540
gacgcgctgc ttaagaacta cgggctgctc tcctgcttca agaaggacct gcacaaggct     600
gagacatacc tgcgggtcat gaagtgtcgc cgcttcgtgg agagcagctg tgccttctag     660
tctaga                                                                666
```

DELIVERY SYSTEM FOR PORCINE SOMATOTROPIN

FIELD OF THE INVENTION

The present invention relates to an expression construct for delivering an exogenous polypeptide to a host. The present invention also relates to recombinant cells which include this expression construct and to semi-permeable capsules which include the recombinant cells.

BACKGROUND OF THE INVENTION

In mammals, somatotropin (growth hormone) is normally secreted from the pituitary gland. However, exogenous administration of somatotropin to pigs has been shown to improve feed efficiency 15–20%, increase daily weight gain 10–15%, reduce carcass fat 10–20%, increase lean meat content 5–10% and reduce feed intake. Unfortunately, somatotropin (which is a small protein of 190 amino acids) is susceptible to gastric acids and protein digestion hence daily injections are required in order to be efficacious. Currently, welfare and ethical issues discourage the use of the pneumatic pST injection gun and the costs of daily administration restrict industry-wide adoption.

Recent advances in gene therapy have enabled the development of strategies which avoid the dependence on autologous target cells and immunosuppressive therapy by utilising transfected cells encapsulated in a semi-permeable alginate-poly-L-lysine-alginate (APA) membrane. The APA capsule environment is compatible with cell viability and growth so that transfected cells remain viable, secreting growth factors, for extended periods. The APA is permeable to small proteins and consequently gene expression can be controlled by external means. The APA barrier inhibits immune surveillance and cell rejection events so that non-host, highly expressing, cells can be employed in the capsule. The APA barrier may also prevent uncontrolled proliferation of the transfected cells in the recipient host. The APA capsule can be removed, potentially re-used, in order to negate the concerns regarding consumption of transgenic material. Further, if the capsule is damaged by severe tissue trauma a normal host-graft rejection would destroy the implanted cells.

SUMMARY OF THE INVENTION

The present inventors have now found that ligation of an insulin secretory signal to a heterologous gene sequence prior to introduction of the gene sequence into a host cell results in a surprising increase in the level of secretion of the heterologous gene product. This finding has led to the development of an improved gene delivery system involving encapsulation of recombinant cells for implantation into a host.

Accordingly, in a first aspect, the present invention provides an expression cassette including a sequence encoding an insulin secretory signal operably linked to a heterologous sequence encoding a polypeptide.

By "heterologous sequence" we mean a sequence other than a sequence encoding insulin.

By "operably linked" we mean that the insulin secretory signal sequence is contiguous and in reading frame with the heterologous coding sequence.

The preferred insulin secretory signal is an insulin secretory signal having the amino acid sequence shown as SEQ ID NO:1. However, it will be appreciated by those skilled in the art that a number of modifications may be made to that secretory signal without deleteriously affecting the biological activity of the signal. For example, this may be achieved by various changes, such as sulfation, phosphorylation, nitration and halogenation; or by amino acid insertions, deletions and substitutions, either conservative or non-conservative (eg. D-amino acids, desamino acids) in the peptide sequence where such changes do not deleteriously affect the overall biological activity of the secretory signal. Thus, the inclusion in the expression cassette of an insulin secretory signal which has been modified in one or more of the abovementioned ways, is to be regarded as being encompassed by the present invention.

The heterologous sequence may encode any polypeptide, other than insulin, of interest. For example, the heterologous sequence may encode a hormone, cytokine, receptor agonist or antagonist, pheromone or enzyme. In a preferred embodiment, the heterologous sequence encodes a growth hormone. Preferably, the growth hormone is somatotropin.

In a second aspect, the present invention provides a vector including an expression cassette of the first aspect. The vector may be any suitable vector for introducing the expression cassette into a cell. Suitable vectors include viral vectors and bacterial plasmids.

The expression cassette of the first aspect of the present invention, or the vector of the second aspect, may further include one or more elements which regulate gene expression. Examples of suitable regulatory elements include the Melatonin Response Element (MRE) (as described in Schrader et al, 1996, the entire contents of which are incorporated herein by reference), and/or rapamycin mediated transcription factors (as described in Magari et al, 1997, the entire contents of which are incorporated herein by reference). In a preferred embodiment, the regulatory element(s) enable pulsatile expression of the polypeptide of interest.

In a third aspect, the present invention provides a recombinant cell which includes an expression cassette according to the first aspect of the present invention.

The recombinant cell may be a bacterial, yeast, insect or mammalian cell. In a preferred embodiment, the recombinant cell is a mammalian cell. In a further preferred embodiment, the cell is a rat myoblast (L6) cell.

In a fourth aspect, the present invention provides a method of producing a polypeptide which includes culturing a recombinant cell of the third aspect under conditions enabling the expression and secretion of the polypeptide and optionally isolating the polypeptide.

The recombinant cell(s) of the present invention may be encapsulated in a semi-permeable matrix for delivery or implantation in a host.

Accordingly, in a fifth aspect, the present invention provides a capsule for implantation in a host, the capsule including a semi-permeable membrane which encapsulates one or more recombinant cells according to the third aspect of the present invention.

In a preferred embodiment, the semi-permeable membrane is an alginate-poly-L-lysine-alginate (APA) membrane. The preparation of an APA semi-permeable membrane is described in Basic et al, 1996, the entire contents of which are incorporated herein by reference.

In a sixth aspect, the present invention provides a method of administering a polypeptide to a host which includes administering to the host an expression cassette according to the first aspect of the present invention.

In a seventh aspect, the present invention provides a method of administering a polypeptide to a host which includes implanting in the host a capsule according to the fifth aspect of the present invention.

The host may be any animal or human. In a preferred embodiment, the host is a livestock animal. In a further preferred embodiment, the host is selected from the group consisting of grazing cattle, feed-lot cattle, dairy cows, pigs and poultry.

It will be appreciated by those skilled in the art that the present invention provides an improved system for the delivery of genetic material to a host. The ligation of the insulin secretory signal to a biologically active polypeptide leads to increased secretion of the polypeptide from recombinant cells. Following secretion, the secretory signal may be cleaved leaving the biologically active polypeptide. The recombinant cells, when encapsulated in a semi-permeable membrane, have the capacity to secrete significant amounts of the biologically active polypeptide and the semi-permeable-membrane enables control of gene expression by external means.

Implantation of the encapsulated recombinant cells provides an advantage in that the implantation requires minimal surgery. Further, the semi-permeable membrane reduces immune surveillance and cell rejection which means that non-host cells can be employed in the capsule.

In a preferred embodiment, the semi-permeable membrane is durable which provides an advantage in that it may limit cell growth thereby preventing uncontrolled proliferation in the recipient host. The capsules provide a further advantage in that they may be removed and re-used.

In order that the nature of the present invention may be more clearly understood, preferred forms thereof will now be described with reference to the following non-limiting Examples and Figures.

BRIEF DESCRIPTION OF THE ACCOMPANYING FIGURES

FIG. 1: (SEQ ID NO:2 and SEQ ID NO: 4) Insulin secretory signal—pST gene construct.

FIG. 2: (SEQ ID NO: 1 and SEQ ID NO: 3) Insulin secretory signal—pST peptide sequence.

FIG. 3: Rate of weight gain (from day 0) for control and individual pST-L6IXS treated pigs.

Figure 4:
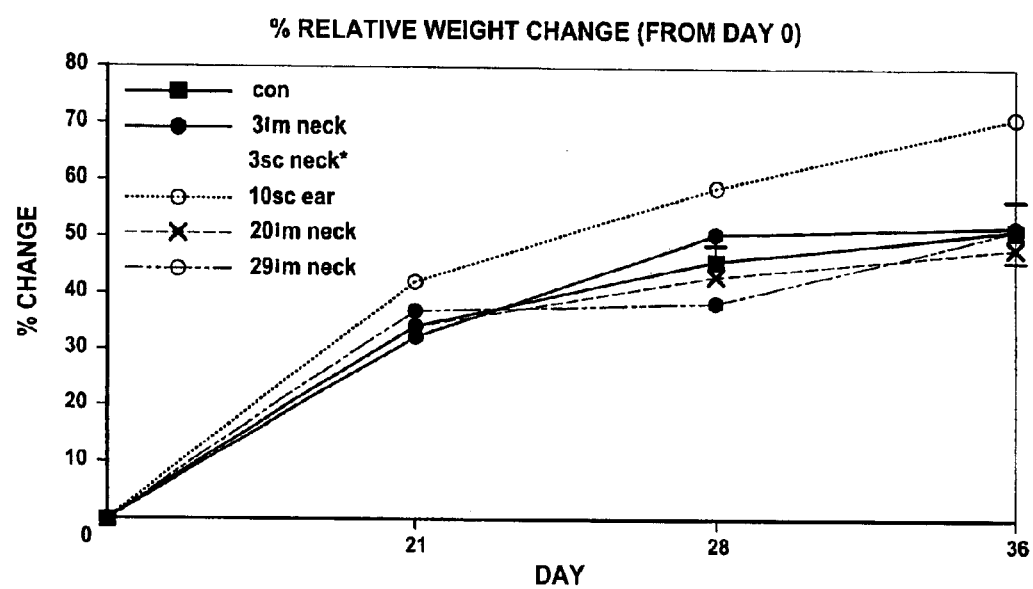

FIG. 4: Percentage weight gain for control and individual pST-L6IXS treated animals.

Figure 5:
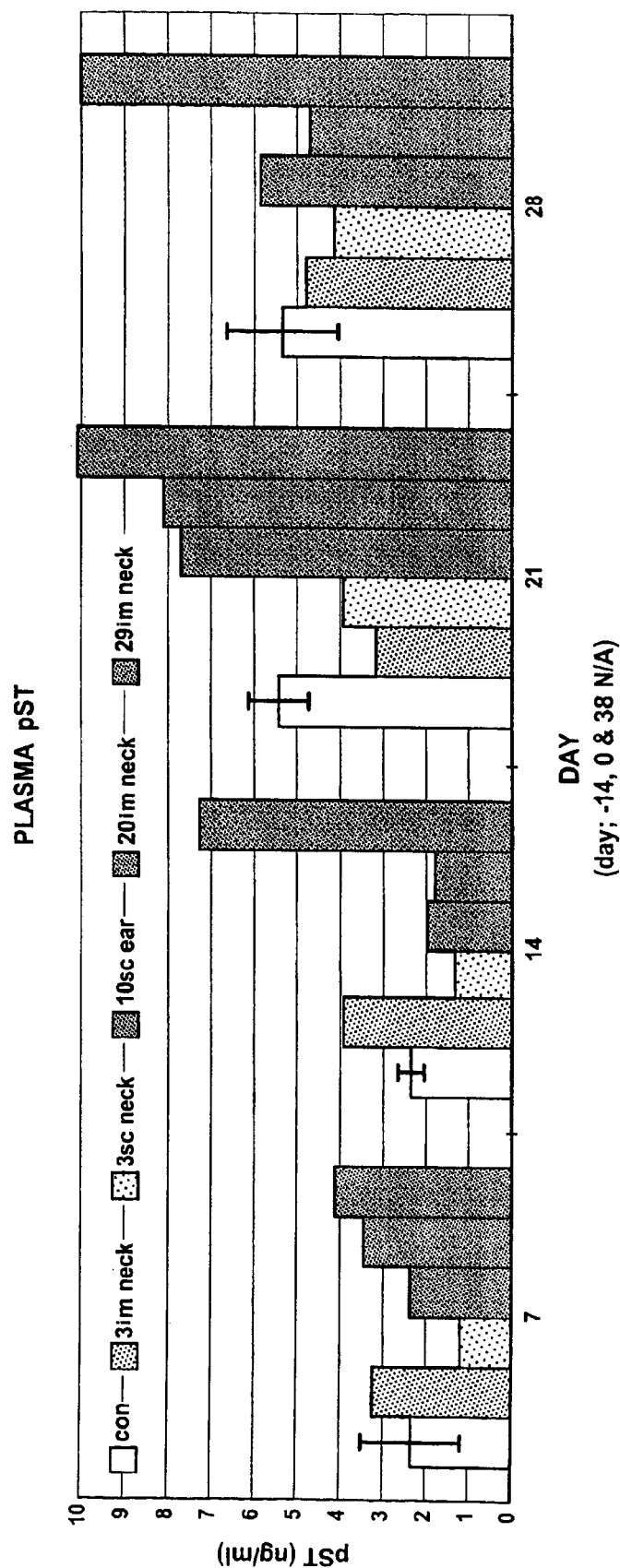

FIG. 5: Plasma, pST levels for control and individual pST-L6IXS treated animals.

FIG. 6: Plate 1—Appraisal of pST-L6IXS capsule administration site

Plate 2—Placement of pST-L6IXS capsule in culture media for ex-vivo assessment.

Figure 7:
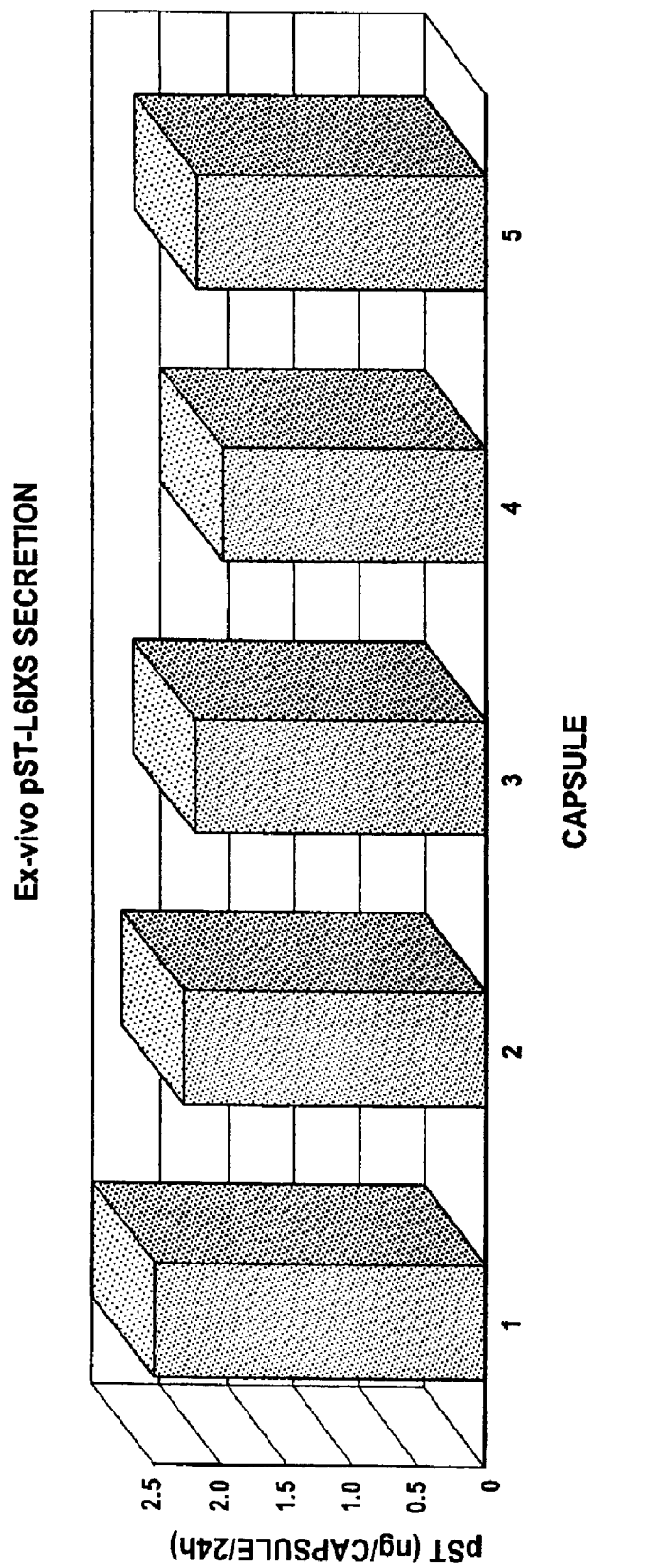

FIG. 7: Ex-vivo assessment of secretion of pST from capsules for a 24 hr period following removal from host animal.

Figure 8:
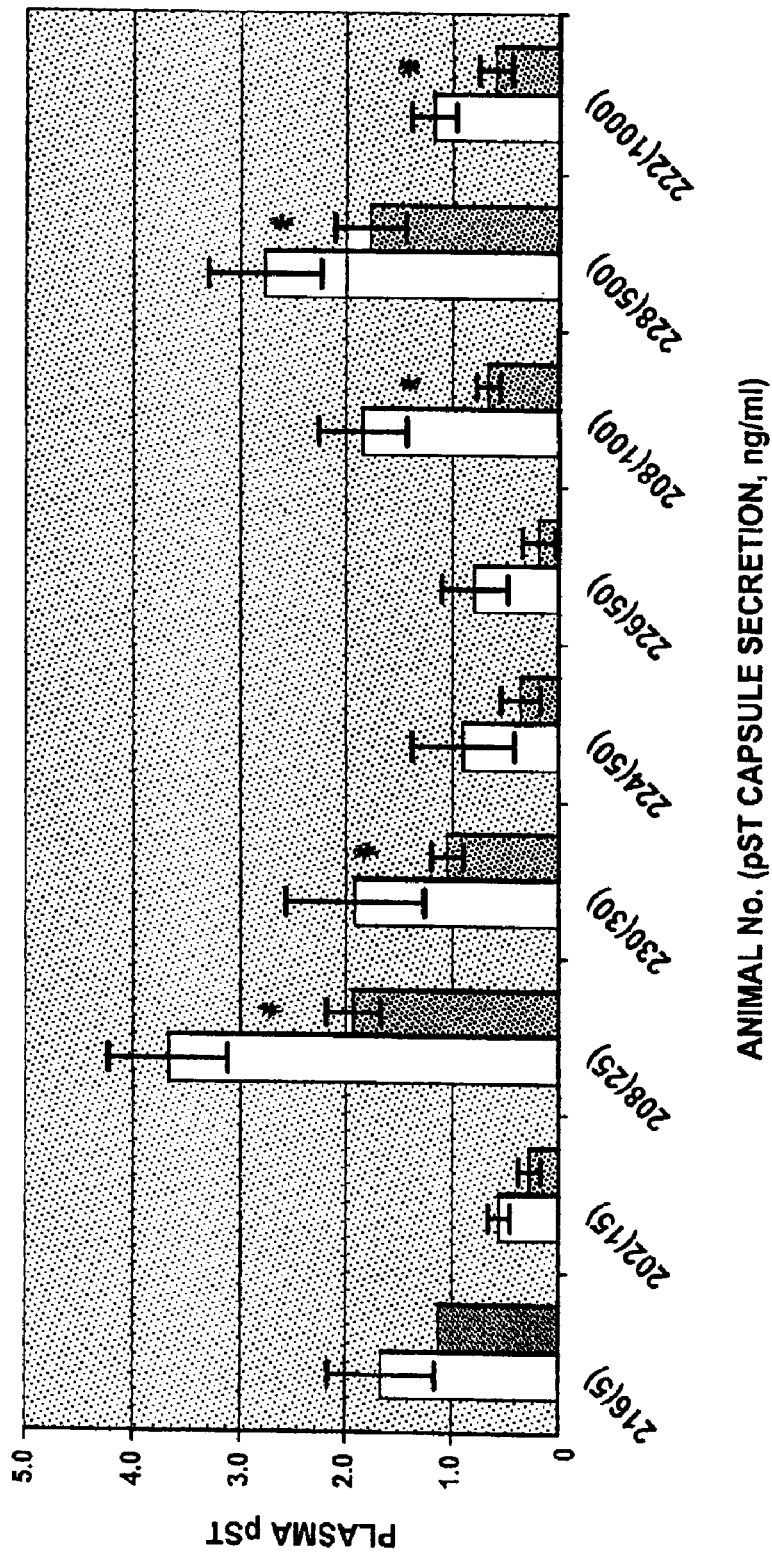

FIG. 8: Mean plasma pST (over 3:hours @ 30 min intervals) before (white bars) and 1 week post pST capsule administration (black bars) (*significant).

Figure 9:
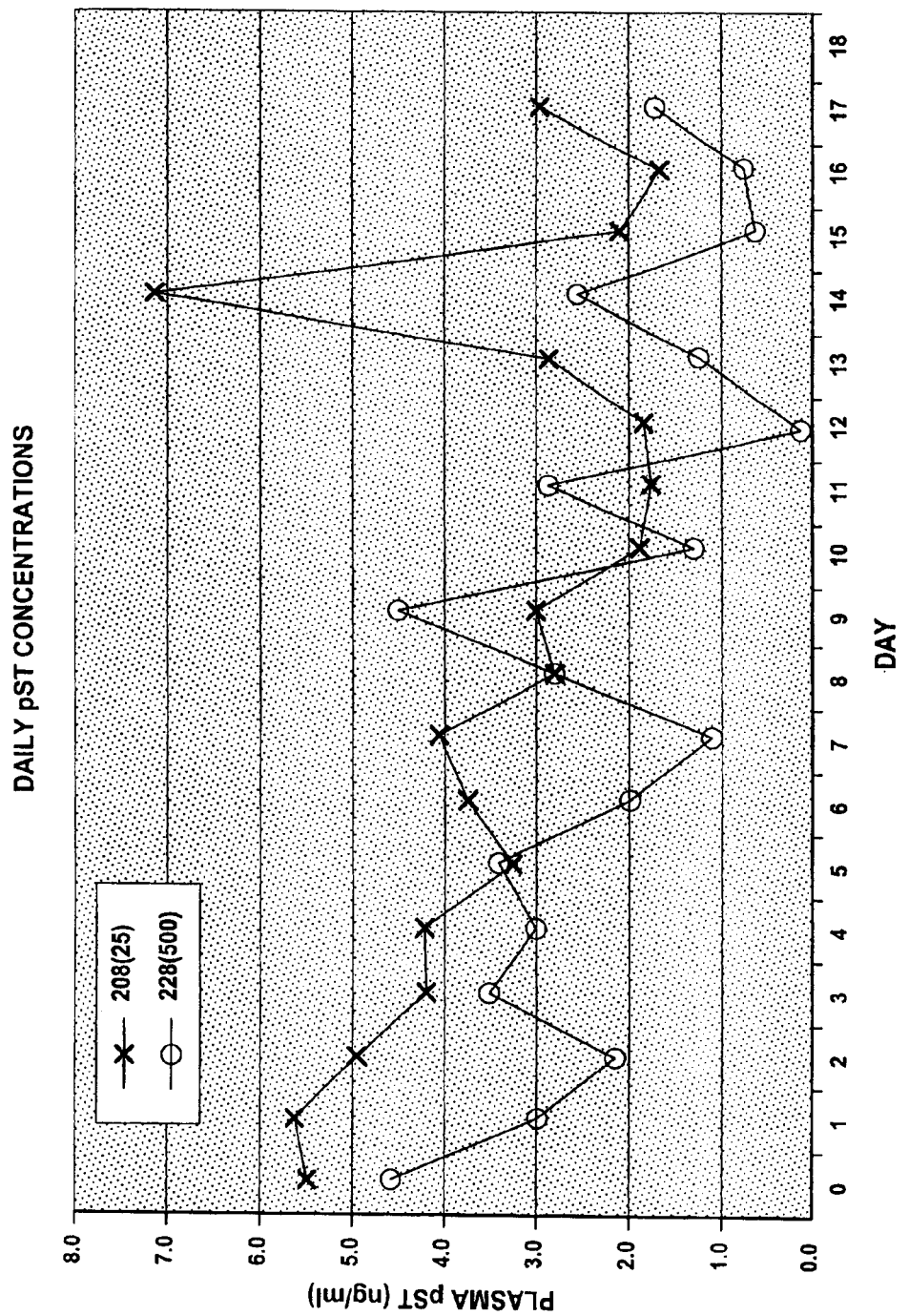

FIG. 9: Daily plasma pST concentrations of two pigs, pig 206 and 228, with implanted capsules secreting 25 ng/ml and 500 ng/ml respectively.

Figure 10:
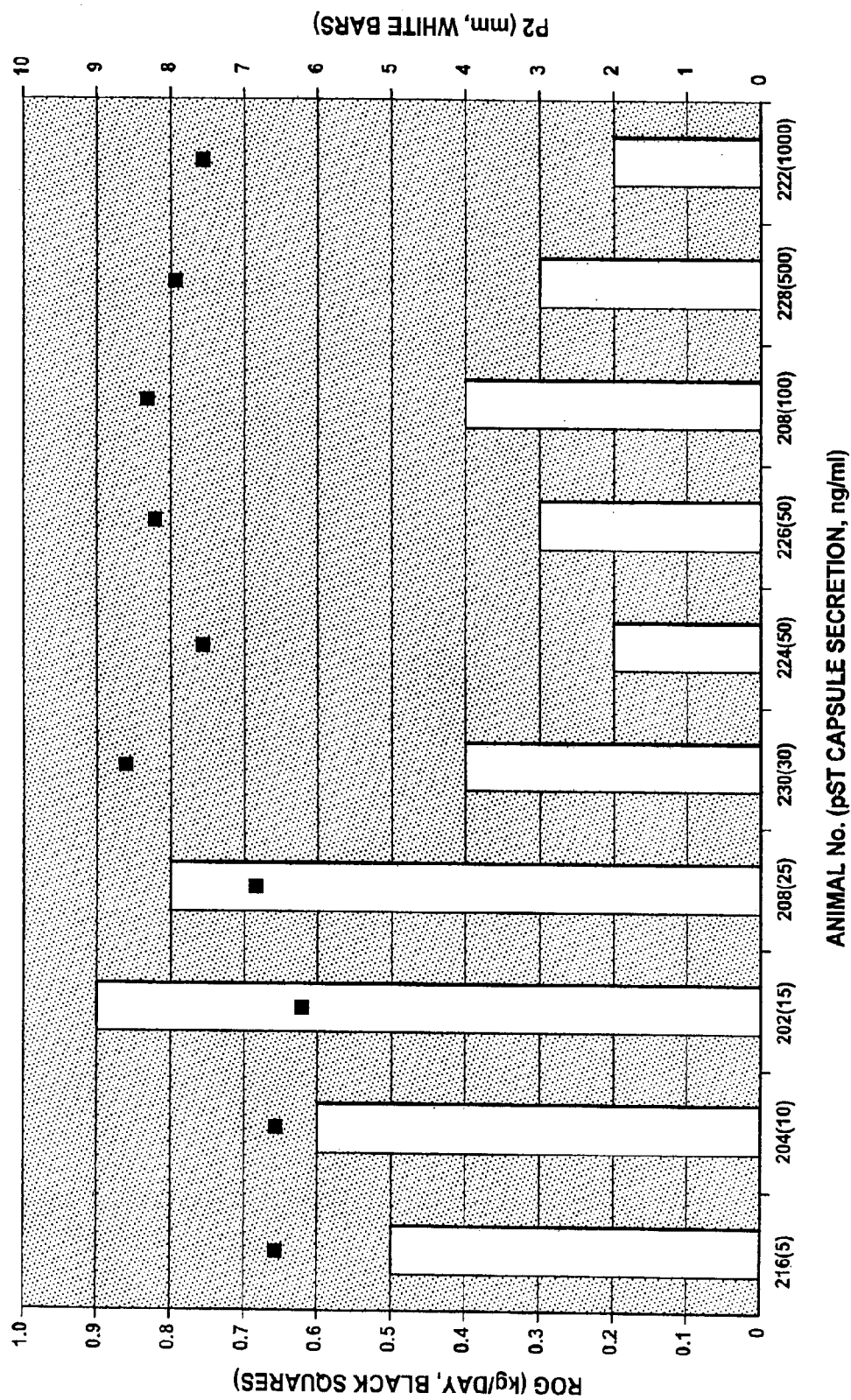

FIG. 10: Rate of Gain (ROG) in kg/day (black squares) and P2 back fat measurements in pigs produced in Example 4.

Figure 11:
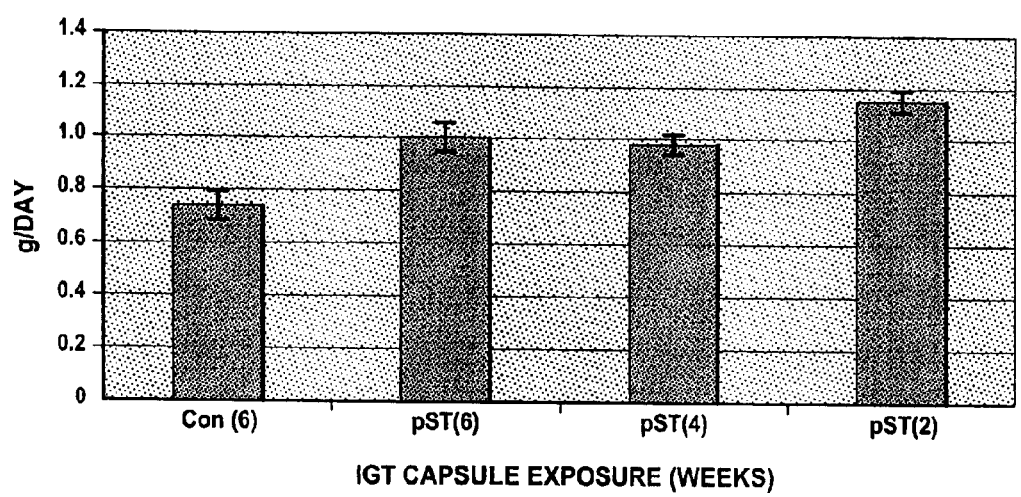

FIG. 11: Rate of Gain (ROG) of male pigs following implantation with pST secreting or control immunoneutral gene therapy (IGT) capsules (±SEM).

Figure 12:
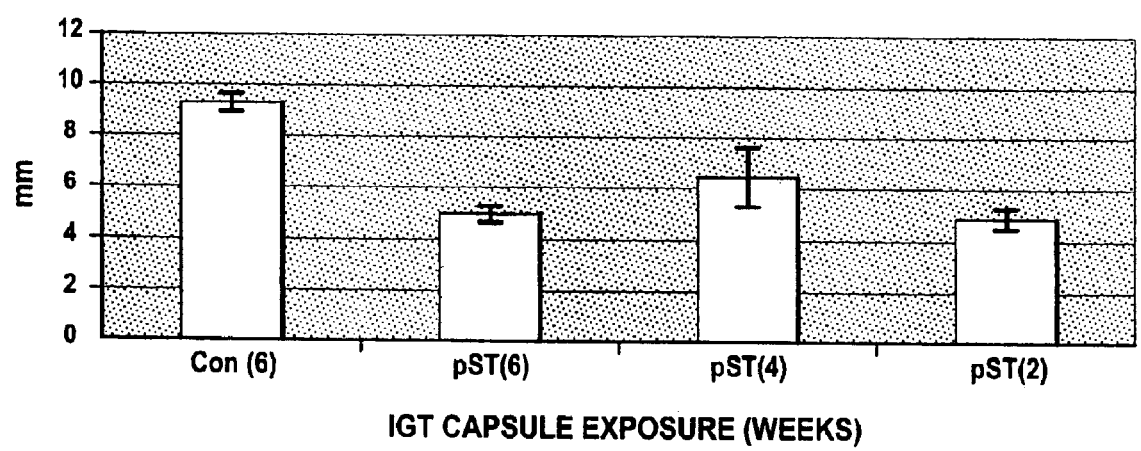

FIG. 12: Back fat (P2) of male pigs following implantation with pST secreting or control immunoneutral gene therapy (IGT) capsules (±SEM).

Figure 13:
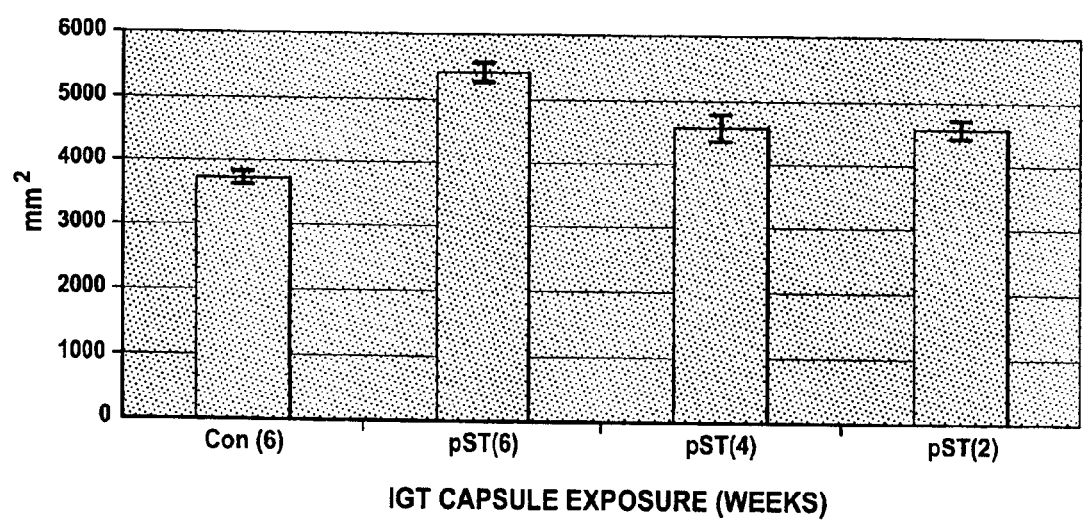

FIG. 13: Loin (eye) muscle area of male pigs following implantation with pST secreting or control immunoneutral gene therapy (IGT) capsules (±SEM).

DETAILED DESCRIPTION OF THE INVENTION

EXAMPLE 1

Cloning of the ISS-PST Construct

The pST gene was obtained from Southern Cross Biotechnology Pty Ltd in an *E. coli* bacterium. The plasmid containing the pST gene, pMG939, was isolated from the bacterium using standard plasmid preparation techniques. The PCR primers were designed to amplify the pST gene, add an Xho I site to the 5' end and an Xba I site to the 3' end to enable ligation events.

The modified pST gene sequence was subsequently ligated to a secretory signal sequence (ISS) derived from the preproinsulin cDNA. Nhe I (GCTAGC) and Xba I (TCTAGA) restriction sites were constructed in front of the ISS start codon and after the 3' terminal codon of pST, respectively, to allow incorporation into the pCI-neo plasmid (Promega). The pST fusion construct was subsequently isolated and sequenced to verify the coding region (FIG. 1).

Transfection of rat myoblast (L6) cells (pST gene incorporation into cells) was performed, with LipoTAXI (Stratagene), 2 hrs after the L6 cells were trypsin treated. pST transfected L6 cell clones were maintained in culture, selected with G418, until >$10^7$ cells were generated. Aliquots (2ml) of the culture supernatant were stored at −20° C. prior to assessment of pST concentrations in a pST radioimmunoassay. (RIA) established by Dr P. Wynn at Sydney University (Camden). The RIA sensitivity was deemed to be >0.4 ng/ml with CV's in the order of 12.4%. The polyclonal antisera was raised in guinea pigs with a pST peptide antigen. The RIA results (Table 1) indicate that the pST gene construct produced protein (FIG. 2) which is recognised by polyclonal antisera raised against the native form of pST, purified from porcine pituitary glands. L6 Clones pCI/pst-1.5 were generated from the modified transfection technique as described below.

Modified Transfection Protocol

Characteristically, L6 cells adhere to culture plates and require detachment with trypsin to passage cells; transfection is routinely performed 24 hrs later. This procedure resulted in L6 cell clones (n=10) secreting pST at 6–18 ng/ml. Applying LipoTAXI (Promega) and the ISS/pST plasmid to the L6 cells 2 hrs after trypsin treatment increased the secretion rate of pST 10–20 fold (>180ng/ml, n=5 clones). This higher pST secretion rates reduce the number of cells (capsules) required to enhance growth.

TABLE 1

Concentrations (ng/ml) for each clone transfected with ISS-pST.

| L6 clone | pST (ng/ml) |
|---|---|
| pCI/pst-1* | 182 |
| pCI/pst-2* | 188 |

TABLE 1-continued

Concentrations (ng/ml) for each clone transfected with ISS-pST.

| L6 clone | pST (ng/ml) |
|---|---|
| pCI/pst-3* | 188 |
| pCI/pst-4* | 140 |
| pCI/pst-5* | 200 |
| pCI/pst-6 | 17 |
| pCI/pst-7 | 12 |
| pCI/pst-8 | 8 |
| pCI/pst-9 | 9 |
| pCI/pst-10 | 7 |
| pCI/pst-11 | 7 |
| pCI/pst-12 | 10 |
| pCI/pst-13 | 8 |
| pCI/pst-14 | 6 |
| pCI/pst-15 | 18 |

EXAMPLE 2

Preparation of the Porcine Somatotropin-rat Myoblast (L1) Immunoneutral Expression System (pST-L6IXS)

The encapsulation procedure described in Basic et al, 1996, was followed with the following modifications.

Encapsulation of cells at room temperature, utilises calcium chloride (or lactate) [100 mM] to gel the alginate [1.5% w/v] droplets followed immediately by washing with saline (0.9% NaCi) then resuspending in poly-L-lysine [0.05%] for 5 min. Calcium chloride crosslinking for 10 min at 37° C. resulted in an alginate matrix that was more compatible with cell viablity.

After the poly-L-lysine coating and saline washes another alginate layer is added. Sodium citrate [55 mM] treatment for 4 min at room temperature softens the capsule to a consistency that increases the difficulty of further manipulation. Cell viablity is apparently reduced to <35% with 4 min exposure to sodium citrate. Placing the capsules in a cell strainer prior to sodium citrate treatment enabled 1 min exposure, at 37° C., improving cell viability to >98%.

Procedural and equipment modifications to the encapsulation protocol improved the efficiency (time and resources) of encapsulation with routine increases in cell viability in the order of 64%.

EXAMPLE 3

Pilot Experiment (1) Involving Implantation of pST-L6IXS in Pigs

Preliminary results obtained with the pST-L6IXS, administered to growing mice, indicate enhanced growth characteristics. In a pilot experiment with male pigs (n=9, mean live weight 61 kg) varying numbers of pST-L6IXS were administered in different sites (3 capsules, i.m. in the neck muscle, 3 capsules s.c. in the neck, 10:capsules s.c. at the base of the ear, 20 capsules i.m. in the neck or 29 capsules i.m. in the neck of individual animals on day 0). Blood samples (10 ml) were collected via jugular venipuncture and P2 ultra-sound (us) measurements were recorded at −14, 0, 7, 14, 21, 28 and 36 days post administration. The sites of pST-L6IXS administration were monitored for tissue reaction events throughout the experiment. On day 36 animals were euthanased and carcass analysis (back fat depth, BF(mm); eyemuscle area, EMA(cm); forearm bone length, BONE(cm); heart weight, HEART(gm); spleen weight, SPLEEN(gm) and liver weight, LIVER(gm) were recorded (see Table 2) and pST-6IXS recovered. FIG. 3 represents the rate of gain (from day 0):for:control (con, mean±SE, n=4) and individual values for pST-L6IXS treated pigs. Percentage weight gain, over the pST-L6IXS treatment is presented in FIG. 4 with the mean±SE for control (con) pigs and individual pST-L6IXS treated animals. Plasma pST (ng/ml) was determined by radioimmunoassay (RIA) and presented in FIG. 5, with mean±SE control (con) and individual concentrations for pST-L6IXS treated pigs. At slaughter the site of pST-L6IXS capsule administration was appraised (FIG. 6, Plate 1, arrow) prior to removal and placement in culture media for ex-vivo assessment (FIG. 6, Plate 2) of 24 hour secretion of pST (FIG. 6). No apparent tissue damage or immune reactions were observed either i.m. or s.c. at day 36. However, the capsules placed in the ear (s.c.) appeared to be highly vascularised and were 100% recoverable. The capsules placed in the neck region were <10% recoverable.

The PST-L6IXS remained patent over 36 days in vivo and appeared to proliferate within the capsule (Plate 2) which can be removed in order to negate the concerns regarding consumption of transgenic material. Further, if the capsule is damaged (i.e. by severe tissue trauma) a normal host-graft rejection destroys the L6 cells preventing propagation of transfected material. Experiments in mice and pigs have demonstrated that pST-L6IXS are efficacious in altering plasma pST, enhancing growth characteristics and potentially immune competence of animals.

TABLE 2 pST-L6IXS PILOT EXPERIMENT:
Pigs (male) supplied by Westmill piggery (Young, NSW)
Experiment at EMAI, maximum security piggery.
ACEC Ref No: 98/20

| | | Treatment | Animal | LIVEWEIGHT (kg) | | | | | | 9/07/98 (slaughter) | CARCASS P2us (mm) | BF (mm) | EMA (cm) | BONE (cm) | HEART (gm) | SPLEEN (gm) | LIVER (gm) |
|---|---|---|---|---|---|---|---|---|---|---|---|---|---|---|---|---|---|
| Pen | | | | Date ### Day −14 | ## 0 | ### 7 | ## 14 | ### 21 | ### 28 | 30 | | | | | | | |
| | A | con | 291 | 24 | 67 | NR | NR | 89 | 95 | 100 | 11 | 9 | 54.5 | 24.5 | 388.6 | 159.8 | 1720.2 |
| C | A | con | 292 | 25 | 61 | NR | NR | 84 | 90 | 90 | 8 | 10 | 54.9 | 23.7 | 381.5 | 103.2 | 1703.8 |
| C | B | con | 294 | 22 | 74 | NR | NR | 94 | 103 | 104 | 12 | 15 | 40.5 | 24.4 | 391.5 | 173.2 | 1636.5 |
| C | B | con | 295 | 22 | 55 | NR | NR | 76 | 84 | 91 | 9 | 7 | 50.6 | 20.0 | 396.6 | 138.2 | 1561.8 |
| T | B | 3sc neck* | 297 | 23 | 67 | NR | NR | 85 | 90 | 91 | 9 | 12 | 45.2 | 23.5 | 385.3 | 177.0 | 1817.7 |
| | | *infected cmpsule site | | | | | | | | CvTp < 0.05 | nsd | nsd | CvTp < 0.06 | nsd | CvTp < 0.05 | nsd | nsd |

EXAMPLE 4

Pilot Experiment (2) Involving Implantation of pST-L6IXS in Pigs

A second pilot experiment was conducted in order to optimise pST-L6IXS delivery by capsules so as to achieve growth responses similar to the energy repartitioning observed with daily pST injections.

As shown in Example 1, pST secreting cells have been produced with a range of secretion rates (6–200 ng/ml). pST secretion rates in the order of 2–25 ng/ml appear to be the most stable following the imposition of stress (i.e. by bacterial contamination) on the pST secreting cells (data not shown). Accordingly, clones secreting about 5 ng/ml (clone pCI/pst-14) and about 10 ng/ml (pCI/pst-12) were selected for this pilot experiment. Male pigs (n=10, mean live weight 78.1 kg) were administered various numbers of capsules (produced according to the procedure described in Example 2) s.c. at the base of the ear (Table 3).

| Pig | Capsule Number | Clone |
| --- | --- | --- |
| 204 | 1 | a |
| 216 | 1 | b |
| 230 | 3 | a |
| 202 | 3 | b |
| 226 | 5 | a |
| 206 | 5 | b |
| 208 | 10 | a |
| 224 | 10 | b |
| 222 | 100 | a |
| 228 | 100 | b | a = clone pCI/pst-14 (5 ng/ml)
b = clone pCI/pst-12 (10 ng/ml)

Body weights were recorded at the beginning and the end of the experiment. Animals were held in individual pens (2 m$^2$) and stabilised to a controlled environment facility (22° C.) for 1 week. The animals were offered ad libitum water and standard pelleted grower rations (3 kg/day @ 09:00 hrs), and daily residues were recorded. Catheters were placed in ear veins (evc), and 24 hours later sampling commenced. Control pig (i.e. no pST capsules) blood plasma (10 ml) was collected every 30 min for 3 hours. pST capsules were administered to the ipsilateral ear immediately following serial sampling. Blood (10 ml) was collected via evc (daily @ 11:00 hrs) while catheters remained patent. Treatment (7 days post administration of pST capsules) blood plasma (10 ml) was collected every 30 min for 3 hours. Slaughter and carcass analysis was performed at about 100 kg live weight 21 days later. pST capsules were then recovered from ears and placed in in vitro culture (for pST assay). The capsule site was also assessed for immune responses (e.g. lymphocyte infiltration).

The results of measurements of mean (3 hr, 30 min interval), plasma pST concentration of pigs before and 7 days after receiving pST capsules (secreting between 5 and 1000 ng/ml) are shown in FIG. 8. As can be seen from FIG. 8, it is apparent that plasma pST is reduced in pigs following 1 week exposure to immunoneutral pST (5–100 ng/ml) secreting capsules.

The variability between and within individual plasma pST concentrations appeared to be more apparent during the control serial sampling period. This phenomenon is reflected in the Standard Errors about the mean observed concentrations. Further, the stable baseline and pST pulse intervals (normally 3–4 hrs) were not recognised by computer programs designed to identify hormone pulses. However, stable baselines and distinct pST pulses were observed in animals 1 week post pST casule administration (FIG. 9).

The Rate of Gain (ROG) shown by the animals appeared to be responsive to pST capsule secretion in a dose dependent manner (FIG. 10). A secretion rate of 30 ng/ml (i.e. 3 capsules secreting 10 ng/ml each) appears to be the minimum dose required to observe growth rate increases. The majority of evc's remained patent for 21 days at which time, the animals were euthanased with barbituate for carcass analysis. Analysis of carcass back fat (P2 without skin) measurements further indicate that 30 ng.ml is the minimum dose to observe energy repartitioning within 21 days of pST capsule administration (FIG. 10).

Throughout the experiment there were no indications of adverse reactions, reduction in weight gain or adverse immune responses, including those animals that received 100 capsules.

EXAMPLE 5

Pilot Experiment (3) Involving Implantation of pST-L6IXS in Pigs

Following example 4, investigations were conducted to assess the effect of the administering optimal pST secretion rates/capsule numbers to pigs at varying times prior to slaughter (i.e. 2, 4 and 6 weeks prior to slaughter) on back fat. 8 pigs were used for each treatment as well as 8 control (i.e. no pST capsules).

The results of the Rate of Gain measurements are provided in FIG. 11.

Back fat measurements were obtained following whole carcass chilling (24 hours @ 4° C.) (FIG. 12). P2 measurements were recorded at the 12$^{th}$ rib 65 mm from the centre of the spinal column. Pigs exposed to capsules secreting pST for 2, 4 and 6 weeks were observed to have significantly reduced back fat. This effect in the 2 and 6 week period is approximately a 46% reduction in back fat. The animals exposed to pST IGT capsules for 4 weeks were more variable in their back fat responses, which may relate to a possible failure to recover all the capsules from a number of these animals.

Loin muscle area in pigs exposed to secreting capsules was only significantly increased (i.e. 22 %) following 6 weeks exposure to pST IGT capsules (FIG. 13).

It will be appreciated by persons skilled in the art that numerous variations and/or modifications may be made to the invention as shown in the specific embodiments without departing from the spirit or scope of the invention as broadly described. The present embodiments are, therefore, to be-considered in all respects as illustrative and not restrictive.

REFERENCES

Basic et al, (1996) Microencapsulation and transplantation of genetically engineered cells: A new approach to somatic gene therapy. Art. Cells, Blood subs. and Immob. Biotech 24(3): 219–255.

Magari et al, (1997) Pharmacological control of humanised gene therapy system implanted into nude mice. J. Clin. Invest. 100: 2865–2872.

Schrader et al, (1996) Identification of natural monomeric response elements of the nuclear receptor R2R/ROR. They also bind to COUP-TF homodimers J. Biol. Chem. 271:19732–19736.

What is claimed is:

1. An expression cassette including a sequence encoding an insulin secretory signal operably linked to a heterologous sequence encoding a mature somatotropin, wherein the insulin secretory signal has the amino acid sequence shown as SEQ ID NO: 1 or is a modified insulin secretory signal which has one or more amino acid modifications of the amino acid sequence shown as SEQ ID NO: 1 and has the same biological activity as an insulin secretory signal having the amino acid sequence shown as SEQ ID NO: 1.

2. An expression cassette according to claim 1, wherein the insulin secretory signal has the amino acid sequence shown as SEQ ID NO:1.

3. An expression cassette according to claim 1 wherein the heterologous sequence encodes a mature porcine somatotropin.

4. A vector including an expression cassette according to claim 1.

5. A recombinant cell which includes an expression cassette according to claim 1.

6. A recombinant cell according to claim 5, wherein the cell is a bacterial, yeast, insect or mammalian cell.

7. A recombinant cell according to claim 6, wherein the cell is a mammalian cell.

8. A mammalian cell according to claim 7, wherein the cell is a rat myoblast (L6) cell.

9. A method of producing somatotropin which includes culturing a recombinant cell of claim 5 under conditions enabling the expression and secretion of the somatotropin and optionally isolating the somatotropin.

* * * * *